(12) United States Patent
Bratosin et al.

(10) Patent No.: US 8,383,406 B2
(45) Date of Patent: Feb. 26, 2013

(54) METHOD FOR STIMULATING THE PROLIFERATION OF DIFFERENTIATED CELLS BELONGING TO THE CHONDROGENIC LINEAGE

(75) Inventors: Daniela Bratosin, Bucharest (RO); Luminita Buia Takacs, Bucharest (RO); Jean Montreuil, Villeneuve d'Ascq cedex (FR); Antoine Heron, Marlenheim (FR)

(73) Assignee: Maco Parma, Mouvaux (FR)

( * ) Notice: Subject to any disclaimer, the term of this patent is extended or adjusted under 35 U.S.C. 154(b) by 320 days.

(21) Appl. No.: 12/682,290

(22) PCT Filed: Oct. 6, 2008

(86) PCT No.: PCT/FR2008/001396
§ 371 (c)(1),
(2), (4) Date: Apr. 9, 2010

(87) PCT Pub. No.: WO2009/080914
PCT Pub. Date: Jul. 2, 2009

(65) Prior Publication Data
US 2010/0256234 A1 Oct. 7, 2010

(30) Foreign Application Priority Data
Oct. 10, 2007 (FR) ..................................... 07 07113

(51) Int. Cl.
*C12N 5/02* (2006.01)
*C12N 5/071* (2010.01)
(52) U.S. Cl. .......................... 435/384; 435/325; 435/378
(58) Field of Classification Search .................. 435/325, 435/378, 384
See application file for complete search history.

(56) References Cited

U.S. PATENT DOCUMENTS
5,468,635 A 11/1995 Komiya et al.

FOREIGN PATENT DOCUMENTS
| JP | 07023780 A * | 1/1995 |
| WO | 9948470 A1 | 9/1999 |
| WO | 0146220 A2 | 6/2001 |
| WO | 2005084684 A1 | 9/2005 |

OTHER PUBLICATIONS

Ohashi-Takeuchi et al. Vesicles with lactate dehydrogenase and without alkaline phosphatase present in the resting zone of epiphyseal cartilage. Biochem. J. (1990) 266, 309-312.*

* cited by examiner

*Primary Examiner* — Taeyoon Kim
(74) *Attorney, Agent, or Firm* — Bachman & LaPointe, P.C.

(57) ABSTRACT

A method for stimulating the proliferation of differentiated cells belonging to the chondrogenic lineage, includes the step of culturing the differentiated cells in a culture medium comprising glycylglycine in an amount sufficient to stimulate the proliferation of the cells.

8 Claims, 2 Drawing Sheets

METHOD FOR STIMULATING THE PROLIFERATION OF DIFFERENTIATED CELLS BELONGING TO THE CHONDROGENIC LINEAGE

BACKGROUND (1) Field of the Invention

The invention relates to a method for stimulating the proliferation of differentiated cells belonging to the chondrogenic lineage in vitro and in vivo, as well as a composition comprising such differentiated cells and a drug for the local treatment of diseases related to the osteoarticular system.

The invention applies to the culturing of cells for therapeutic purposes, in particular the culturing of chondrocytes, with a view to the treatment of osteoarthritic lesions, as well as to drugs intended for the treatment of osteoarthritic lesions.

(2) Prior Art

The culturing of chondrocytes is currently an important issue, in particular within the framework of tissue regeneration in human and veterinary medicine. As a matter of fact, the autologous transplantation of cartilage cells into a diseased tissue is an advantageous method of treating diseases of the cartilage, e.g., such as osteoarthritis.

As a matter of fact, in order to avoid the use of an invasive method for total replacement of osteoarthritic joints, cartilage cells are taken from the patient and then cultured in vitro in a chondrocyte expansion medium, so as to be multiplied and finally re-implanted in the tissue. The portion of the joint affected by osteoarthritis is thus reconstructed and grafted onto the healthy portion.

Chondrocyte culture mediums generally comprise a base medium of the DMEM type, foetal calf serum or foetal bovine serum (FBS), and possibly other elements such as a mixture of antibiotics. The document U.S. Pat. No. 6,558,949 proposes an improved culture medium for chondrocytes comprising growth factors and in which the FBS is replaced by human serum. This medium enables the proliferation speed of the chondrocytes to be increased but does not significantly improve the proliferation rate.

Methods of improving cell proliferation have been developed in the field of cellular engineering. The document WO 01/46220, in particular, proposes the addition of small peptides, particularly oligopeptides comprising 3 to 5 amino acids, in order to increase the cellular viability of cells used for the production of antibodies or proteins of interest.

In this document, WO 01/46220, it appears that the addition of glycine monomer or diglycine to the culture medium only very slightly increases the proliferation of hybridoma cells in comparison with that obtained in a non-supplemented culture medium, whereas the addition of a tri- tetra- or pentapeptide of glycine increases cell proliferation significantly.

SUMMARY OF THE INVENTION

Contrary to the results presented in this document, in the case of hybridoma cells of mice, the applicant observed that the glycylglycine added to the chondrocyte culture medium surprisingly led to a large-scale production of these cells. In particular, the proliferation rate of the chondrocytes in such a medium is multiplied by three, and even by seven, in comparison with that obtained in a non-supplemented culture medium.

According to a first aspect, the invention relates to a method for stimulating the proliferation of differentiated cells belonging to the chondrogenic lineage, comprising the culturing of said differentiated cells in a culture medium comprising glycylglycine in sufficient quantity to stimulate proliferation of the cells.

In particular, the invention proposes a method of stimulating the proliferation of the differentiated cells belonging to the chondrogenic lineage, in a culture medium comprising 1 to 500 mM of glycylglycine and preferably 10 to 50 mM of glycylglycine.

According to a second aspect, the invention proposes a composition comprising differentiated cells belonging to the chondrogenic lineage and a culture medium incorporating glycylglycine.

According to a third aspect, the invention proposes a drug for the local treatment of diseases related to the osteoarticular system, by stimulating the proliferation of the differentiated cells belonging to the chondrogenic lineage, said drug including glycylglycine.

Finally, according to a fourth aspect, the invention relates to the use of glycylglycine for the preparation of a drug intended for in situ treatment of diseases related to the osteoarticular system, by stimulating the proliferation of the differentiated cells belonging to the chondrogenic lineage.

BRIEF DESCRIPTION OF THE DRAWINGS

Other objects and advantages of the invention will become apparent over the course of the following description, with reference to the appended drawings, in which.

DETAILED DESCRIPTION OF THE PREFERRED EMBODIMENT(S)

Figure 1A:
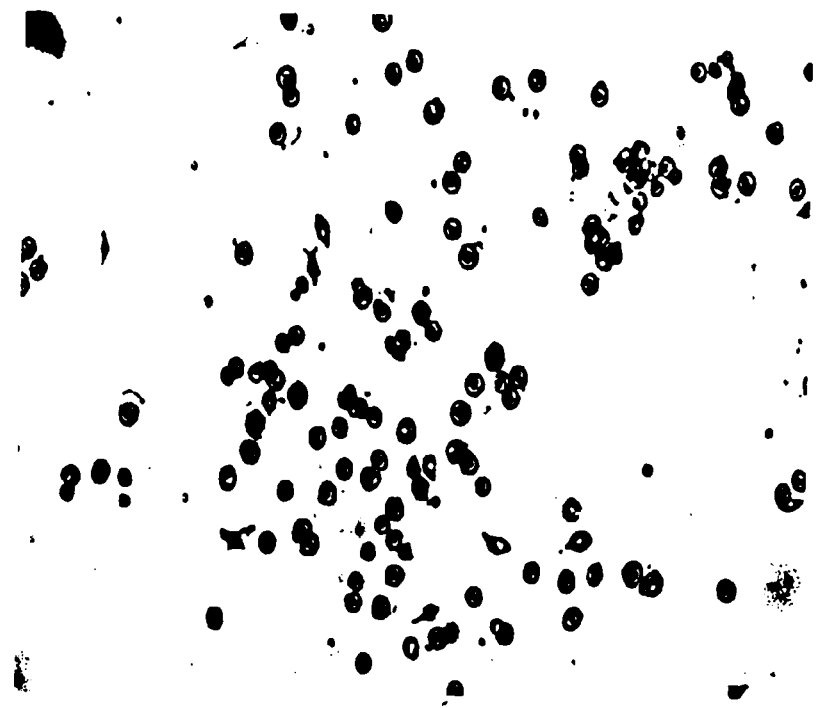
FIGS. 1A and 1B show microscopic observations of human osteoarthritic chondrocytes cultured for 7 days under identical conditions, in the absence (A) and presence (B) of 20 mM glycylglycine.

According to a first aspect, the invention relates to a method for stimulating the proliferation of differentiated cells belonging to the chondrogenic lineage, comprising the culturing of said differentiated cells in a culture medium comprising glycylglycine in sufficient quantity to induce proliferation of the cells.

The method for stimulating the proliferation of the differentiated cells is carried out in vitro, e.g., after sampling cartilage from the patients.

Differentiated cells belonging to the chondrogenic lineage are cells capable of synthesizing type-II collagen or aggrecan from an endogenous gene.

For example, the differentiated cells are chondrocytes extracted from cartilage tissues which are healthy or affected by osteoarthritis.

Alternatively, the chondrocytes are differentiated in vitro from progenitors such as mesenchymatous strain cells.

The method according to the invention leads to large-scale production of the chondrogenic cells, i.e., a cell population at least 2 times greater than the original population, and in less than 5 days.

Furthermore, the method enables the phenotype of the cultured chondrocytes to be preserved. As a matter of fact, the presence of glycylglycine blocks the dedifferentiation of the chondrocytes into fibroblasts.

In particular, by using the method according to the invention, the chondrocyte proliferation rate is multiplied by three or even seven, in comparison with that obtained in a non-supplemented standard culture medium, for a single culture period.

In one particular embodiment, and prior to culturing in a medium comprising glycylglycine, the chondrocytes are isolated from the osteoarthritic cartilage.

The method for stimulating the proliferation of the chondrocytes includes a step of culturing the chondrocyte cells for one to seven days, and in particular less than five days, in a base medium of the DMEM type by Dulbecco, possibly comprising antibiotics and antimycotics (penicillin, streptomycin, amphotericin), L-glutamine and foetal calf serum, the medium being supplemented with glycylglycine.

According to one embodiment, the culture medium includes from 1 to 500 mM of glycylglycine, particularly 10 to 50 mM of glycylglycine and even more particularly 20 mM of glycylglycine.

In particular, the culture medium does not contain any added growth factors other than the glycylglycine. Since the growth factors used in culture mediums are generally complex and costly synthetic molecules, a medium devoid of such molecules is therefore a particularly advantageous alternative.

The cell proliferation can be carried out from healthy or diseased cells. The interest is particularly great in the case where the proliferation is carried out from diseased chondrocytes.

As a matter of fact, it has recently been shown that cartilage cells derived from patients who are elderly or affected by osteoarthritis were capable of generating new cartilage. This method is therefore particularly advantageous when the tissue is affected to such an extent that only diseased cells can still be sampled. These cells can be extracted and then cultured in a culture medium according to the invention.

According to a second aspect, the invention relates to a composition comprising differentiated cells belonging to the chondrogenic lineage and a culture medium including glycylglycine.

As already known, the cultured and multiplied chondrocytes are re-implanted into the diseased tissue of the patient. The surgeons who perform these types of procedures prepare an appropriately shaped substitute for the cartilage, which corresponds precisely to the osteoarthritic lesion.

To accomplish this, one re-implantation method consists in culturing the chondrocytes in an artificial porous biomaterial such as a collagen or chitosan sponge so as to give the graft a shape which is customized to the lesion. The collagen sponge supporting the graft is then surgically applied to the lesion. Such a sponge, for example, is described in the document RO 114560.

According to the invention, the chondrocytes are cultured on an artificial porous biomaterial in a glycylglycine-supplemented culture medium.

An advantage provided by the invention is that the presence of glycylglycine prevents the dedifferentiation of the chondrocytes into fibroblasts, a phenomenon which is generally observed beyond five days of culturing.

Furthermore, since the proliferation is markedly faster than that observed in the case where a medium is used which is not supplemented with glycylglycine, the cells quickly become rather numerous and can be re-implanted after only three days of culturing, thereby enabling significant savings to be achieved.

The invention further relates to a drug including glycylglycine, for the local treatment of diseases related to the osteoarticular system, such as osteoarthritis. The drug acts by stimulating the proliferation of the differentiated cells belonging to the chondrogenic lineage. This local release of a factor capable of mobilising the chondrocytes (local trophic effect) constitutes a novel treatment strategy.

The drug is used in human and veterinary medicine, in particular for treating osteoarthritic lesions of horses.

According to a first alternative, the drug is in the form of an injectable solution of glycylglycine dissolved in an acceptable solvent, for direct injection into the osteoarthritic joint. An example of an acceptable solvent is an injectable physiological serum containing 0.9% NaCl. The injectable solution can, in particular, contain 1 to 500 mM of glycylglycine.

An injectable drug for the local treatment of osteoarthritis is particularly advantageous because it enables a damaged joint to be reconstructed while at the same time limiting invasive surgical procedures.

Under the effects of the glycylglycine solution injected directly into the osteoarthritic joint, the chondrocytes multiply and replace the damaged portion of the joint.

According to a second alternative, the drug consists of an implantable material into which glycylglycine is incorporated, which is intended to replace the damaged portion of the cartilage. This material, which, for example, can be a collagen sponge, can be directly re-implanted into the cartilage without carrying out the preliminary step of culturing the chondrocytes.

According to this alternative, the damaged portion of the cartilage is extracted and replaced by a collagen sponge comprising a composition of glycylglycine. The collagen sponge causes a progressive salting-out of the glycylglycine and thereby mobilises the healthy chondrocytes present at the periphery of the sponge.

Under the effects of the glycylglycine, the healthy chondrocytes multiply and colonise the collagen sponge until reaching a cell density similar to the density of the surrounding cartilage.

The advantage of this alternative is that it requires only a single surgical step, given that the collagen sponge can be prepared in advance and implanted into the joint as soon as the damaged portion has been removed.

In another alternative, the implantable material comprising the glycylglycine likewise comprises chondrocytes.

The presence of the glycylglycine in the implantable material makes it possible to maintain the capability of the chondrocytes contained in the sponge to continue proliferating in situ after the graft, in order to more quickly reach the optimal cell density for the cartilage.

According to a final aspect, the invention thus concerns the use of glycylglycine for in situ treatment of diseases related to the osteoarticular system, by stimulating the proliferation of the differentiated cells belonging to the chondrogenic lineage.

The invention will be better understood from example 1, which provides a detailed description of the culturing of chondrocytes according to the method and object of the invention, as well as from the following characterising examples of the large-scale production of chondrocytes.

Materials and Methods

Dulbecco's medium DMEM was supplied by Cambrex Bio Science (Verniers, Belgium), the foetal calf serum, penicillin, streptomycin, amphotericin B and the L-glutamine (Invitrogen), the PKH 26, hyaluronidase, trypsin, collagenase of *Clostridium histolyticum* and the calcein-AM by SIGMA (St. Louis, USA), and the N-glycylglycine by BACHEM (Villers-le-Bretonneux, France). Replicative senescence was studied using the C12FDG (5-dodecanoylaminofluorescein di-β-D-galactopyranoside) supplied by Molecular Probes (Eugen, USA). The cytofluorimeter was a Becton-Dickinson FACScan instrument (San Jose, USA) equipped with CellQuest Pro software.

EXAMPLES

Example 1

Isolation and Culturing of the Chondrocytes

Example 1.1

Isolation of the Chondrocytes

The articular cartilage was sampled under sterile conditions from an osteoarthritic patient. The chondrocytes were isolated according to the methods of Green (1971) and Kuettner et al (1982), by enzymatic dissociation of the cartilage in Dulbecco's DMEM medium supplemented with a mixture of antibiotics and antimycotics (10 U/ml penicillin, 10 mg/ml streptomycin, 0.025 mg/ml amphotericin B), 2 mM L-glutamine and 10% foetal calf serum. The cartilage was cut up into small fragments and incubated (37° C.; 20 min) in the aforegoing DMEM medium containing 1 mg/ml of sheep testicular hyaluronidase. The fragments were next washed in PBS buffer (Phosphate Saline Buffer) with a pH of 7.4, and then incubated (60 min, at 37° C.) in the same buffer containing 0.25 g/100 mL trypsin. The fragments of cartilage previously washed with the PBS buffer with a pH of 7.4 were finally dissociated via incubation (15 hrs at 37° C.) in the DMEM medium containing 0.2% collagenase of *Clostridium histolyticum* and 10% foetal calf serum. The cells were collected by centrifugation (15 min, 3000 g), washed 2 times with the complete DMEM medium and cultured under the conditions hereinbelow.

Example 1.2

Culturing of the Chondrocytes

The chondrocytes were cultured on uncoated culture plates with polystyrene wells, at 37° C. for 1 to 7 days in a $CO_2$ atmosphere (5%), in the absence or presence of 20 mM of glycylglycine, in a DMEM medium containing 10% foetal calf serum supplemented with a mixture of antibiotics and antimyotics (10 U/ml penicillin, 10 mg/ml streptomycin, 0.025 mg/ml amphotericin B) and 2 mM L-glutamine. With a view to subsequent cytometric analyses, the chondrocytes were detached by incubating for 3 minutes in a pH 7.4 PBS buffer solution of trypsin (0.25 g/100 ml) and EDTA (0.2 g/100 ml) kept at 37° C. After 3 washings with PBS buffer at pH 7.4, and after counting the cells using a Malassez chamber, the chondrocytes were subjected to various flow cytometry analyses described hereinbelow.

Figure 1B:
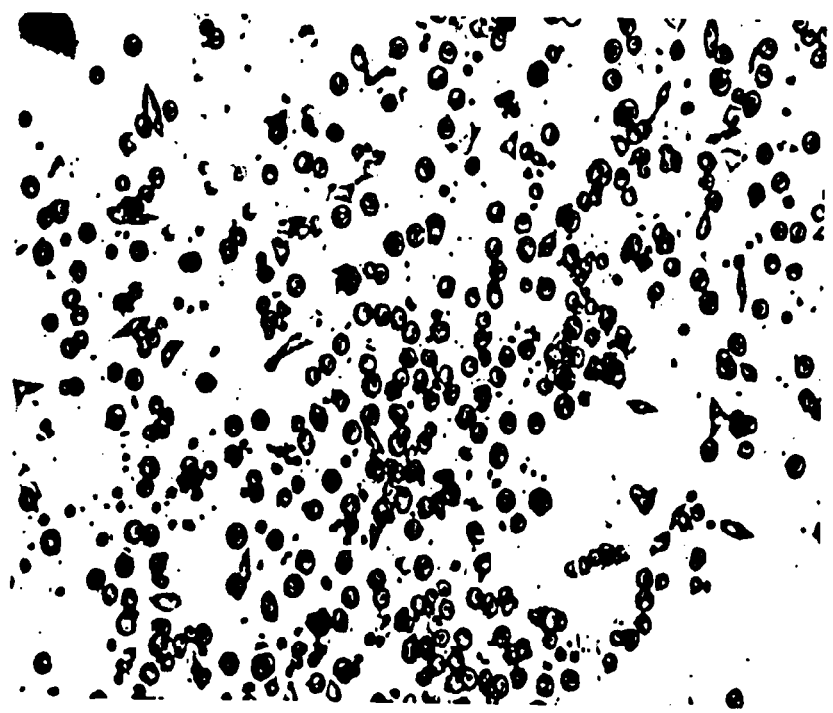

FIGS. 1A and 1B show this large-scale production of the chondrocytes. FIG. 1A is a microscopic observation of chondrocytes cultured in a DMEM medium such as the one described above, without glycylglycine. FIG. 1B is a microscopic observation of chondrocytes cultured in a DMEM medium identical to that of FIG. 1A, but in the presence of 20 mM of glycylglycine.

According to FIGS. 1A and 1B, counting the cells makes it possible to determine that the proliferation rate of the chondrocytes cultured in the DMEM medium supplemented with 20 mM of glycylglycine is multiplied by three in comparison with that obtained in an identical culture medium not supplemented with glycylglycine.

Example 2

Flow Cytometry Analysis

The analyses were carried out using an FACScan cytometer equipped with ProCellQuest software, under the following experimental conditions: cells in suspension in a PBS isotonic buffer at pH 7.4, having an osmolality of 320-330 mOsmol/kg, with the number of cells analysed being 10,000.

Example 2.1

Cell Proliferation Test

Principle—Prior to being cultured, the chondrocytes were irreversibly labelled with a vital fluorescent membrane intercalator derived from arcidine orange, the PKH-26, with a view to following cell proliferation via flow cytometry, which entails a decrease in the overall fluorescence of the cells.

Operating procedure—$10^6$ chondrocytes in suspension in 1 ml of the "diluent C" of the labelling kit are added to 1 ml of a 2 μm solution of PKH-26 in the same diluent. After 4 min of incubation at ambient temperature, the reaction is stopped by the addition of 2 ml of foetal calf serum and then, after incubating for one minute, 4 ml of complete DMEM medium are added. After centrifuging (5 min, 2000 g at 25° C.), the resulting sediment is washed 3 times with 10 ml of complete DMEM medium. The cells are then cultured for 3 days under the conditions described in example 1.2, detached from the support thereof according to the above-described method, placed back in suspension in a PBS buffer at pH 7.4 and analyzed by flow cytometry in the logarithmic mode FL2.

Figure 2:
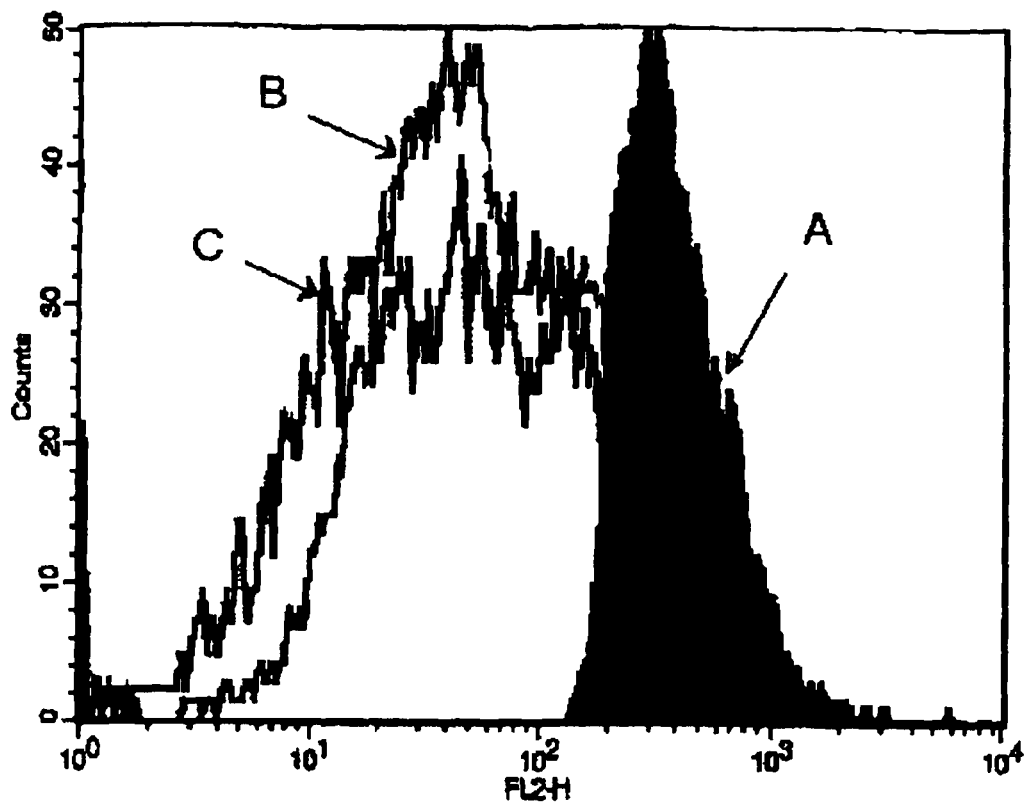
FIG. 2 shows a cytofluorimetric test of human osteoarthritic chondrocyte proliferation using PKH-26.

FIG. 2 shows the results of the flow cytometry analysis of the proliferation rate of the human osteoarthritic chondrocytes labelled with PKH-26 and cultured in the presence and absence of 20 mM glycylglycine.

Curve A shows the fluorescence of the chondrocytes labelled prior to culturing, i.e., prior to division of the cells. Curve B shows the fluorescence of the chondrocytes cultured in a DMEM medium as described above, in the absence of glycylglycine. Curve C shows the fluorescence of the chondrocytes cultured in a DMEM medium supplemented with 20 mM of glycylglycine.

The cells initially labelled with the PKH-26 have a high fluorescence intensity (curve A). This intensity decreases over the course of the cell division since the PKH-26 is then distributed between the cells derived from the division. It is clearly apparent that the intensity of the fluorescence of the chondrocytes after culturing (curves B and C) is lower than the fluorescence of the cells prior to culturing. This confirms the fact that cell divisions have indeed occurred and that the proliferation was effective.

The comparison between curves B and C likewise enables it to be established that the fluorescence is further decreased in the case of a population of chondrocytes cultured in the DMEM medium described above, which is supplemented with glycylglycine. This illustrates clearly that the cell divisions were more numerous in this case than during the culturing of chondrocytes in a DMEM medium not supplemented with glycylglycine.

Example 2.2

Proliferation Rate of the Cells

Glycylglycine Concentration Kinetics

The table below compiles the proliferation rates of cells cultured in the absence or presence of various concentrations of glycylglycine.

In order to carry out this test, 76,000 cells were cultured for three days under the culture conditions presented below.

| Concentration of Gly-Gly (mM) | Number of cells obtained (cells/ml) | Proliferation rate after 3 days | Proliferation rate/culture medium without Gly-Gly |
|---|---|---|---|
| 0 | 90,000 | 18% | 1 |
| 20 | 190,000 | 150% | 2.11 |
| 50 | 124,000 | 63% | 1.38 |
| 100 | 145,000 | 91% | 1.61 |
| 200 | 130,000 | 71% | 1.44 |
| 500 | 112,000 | 47% | 1.24 |

Other chondrocyte cultures carried out for five days with a glycylglycine concentration of 20 mM provided proliferation rates 3 to 5 times higher than the proliferation rate observed after culturing in a medium not supplemented with glycylglycine.

Example 2.2

Calcein Test

Viability and Cytotoxicity of the Cells

The viability of the chondrocytes and the toxicity of the peptide were studied using the method developed by Bratosin et al (2005) and based on measuring the cellular esterase activity by means of calcein-AM.

Principle—Calcein-AM is a non-fluorescent acetic ester of fluorescein which passively passes through the membranes of the viable cells and is transformed by the cytosolic esterases into fluorescent calcein, which provides an intense green signal at 530 nm and which is retained only by the cells having an intact plasma membrane. The disappearance of calcein thus indicates both the decrease in the characteristic esterase activity of the senescent cells, undergoing apoptosis or subjected to the action of toxic substances, and the leakage of this compound from the cells due to the permeabilisation of the membrane thereof. These two complementary mechanisms make calcein-AM an excellent test of cell viability and cytotoxicity.

Operating procedure—The chondrocytes ($4\times10^5$) in suspension in 200 µl of PBS buffer at pH 7.4 are incubated (45 min at 37° C.) in darkness, in the presence of 5 µM calcein-AM. Next, 0.5 ml of PBS buffer at pH 7.4 is added to the suspension, which is immediately analysed by flow cytometry in the FL1 logarithmic mode (number of cells counted: 10,000).

Figure 3:
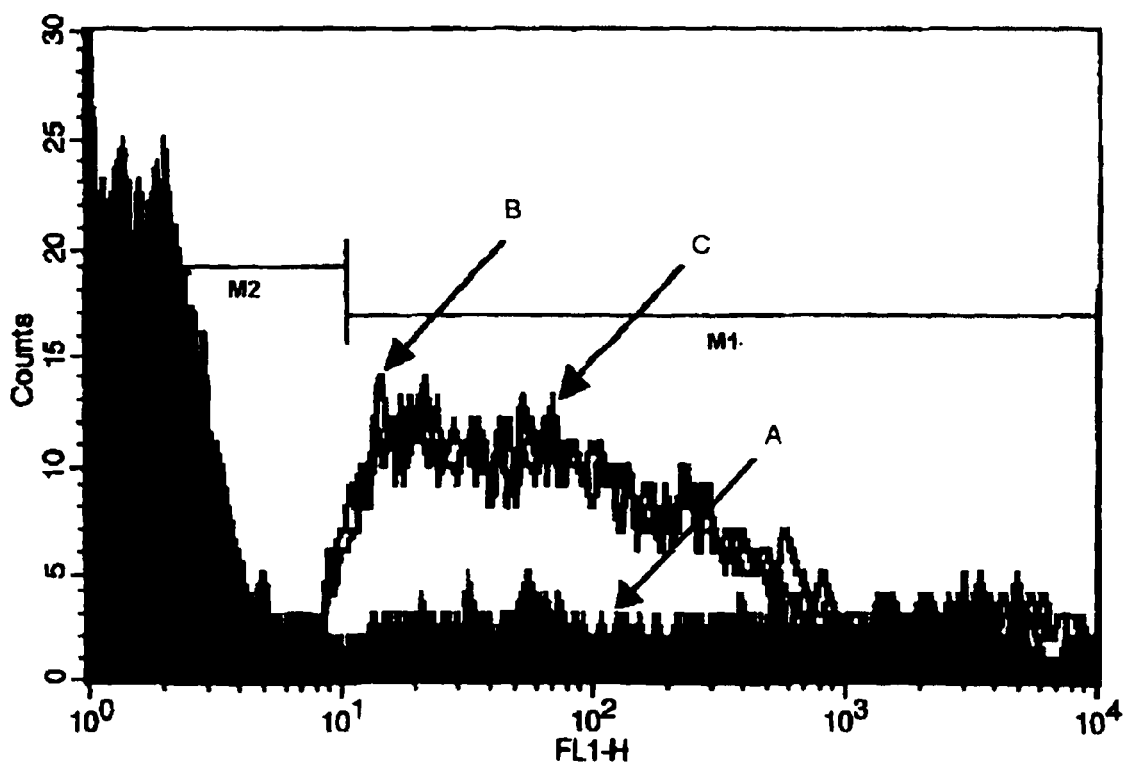
FIG. 3 shows a cytofluorimetric viability test, using calcein-AM, for human osteoarthritic chondrocytes cultured for 7 days in the absence and in the presence of 20 mM glycylglycine and adhering to the growth medium.

FIG. 3 shows the test results with calcein. The intensity of the fluorescence on a logarithmic scale is plotted on the x-axis and the relative number of cells is plotted on the y-axis. Curve A, produced at time zero of the culture, shows that the suspension of chondrocytes taken from the osteoarthritic cartilage contains a significant proportion (75%) of dead cells. Curve B shows the number of viable chondrocytes after culturing in a DMEM medium such as the one described above, without glycylglycine. Curve C shows the number of viable chondrocytes after culturing in a DMEM medium identical to that of curve B, in the presence of 20 mM of glycylglycine.

Curves B and C are superimposable, thereby demonstrating that the glycylglycine added to the culture medium is not toxic to the chondrocytes and does not reduce the viability thereof. This non-toxicity makes it possible to anticipate the use of glycylglycine in vivo, for stimulating the proliferation of the chondrocytes, and more generally the differentiated cells of the chondrogenic lineage.

The invention claimed is:

1. A method for stimulating a proliferation of chondrocytes, comprising the step of: culturing said chondrocytes in a chondrocyte culture medium comprising a base medium and serum, and supplemented with glycylglycine in sufficient quantity to stimulate proliferation of the chondrocytes.

2. The method of claim 1, further comprising providing the chondrocyte culture medium with 1 to 500 mM of glycylglycine.

3. The method of claim 2, further comprising providing the chondrocyte culture medium with 10 to 50 mM of glycylglycine.

4. The method of claim 3, further comprising providing the chondrocyte culture medium with 20 mM of glycylglycine.

5. The method of claim 1, wherein the chondrocyte are isolated from osteoarthritic cartilage.

6. The method as claimed in claim 5, further comprising isolating the chondrocytes by enzymatic dissociation of the cartilage.

7. The method as claimed in claim 1, further comprising culturing the cells for a period of one to five days.

8. The method as claimed in claim 1, further comprising culturing the cells on an artificial porous biomaterial.

* * * * *